United States Patent [19]

Rubens

[11] 4,222,389
[45] Sep. 16, 1980

[54] OBJECTIVE DETERMINATION OF THE RATE OF OXYGEN UTILIZATION IN PERIPHERAL TISSUE

[75] Inventor: Harry E. Rubens, New York, N.Y.

[73] Assignee: Institute of Applied Biology Special Cancer Research Project, Bay Harbor Islands, Fla.

[21] Appl. No.: 843,270

[22] Filed: Oct. 18, 1977

[51] Int. Cl.$^2$ .............................................. A61B 6/00
[52] U.S. Cl. .................................... 128/633; 128/666; 356/41
[58] Field of Search .............. 128/2 L, 2 A, 2 R, 2 G, 128/2.07, 633, 637, 666; 356/39–41

[56] References Cited

U.S. PATENT DOCUMENTS

| | | | |
|---|---|---|---|
| 2,824,972 | 2/1958 | Beitz | 356/308 X |
| 3,152,587 | 10/1964 | Ullrich et al. | 128/2 L |
| 3,486,822 | 12/1969 | Harris | 356/308 |
| 3,810,460 | 5/1974 | Van Nie | 128/2 L X |
| 4,000,972 | 1/1977 | Braun et al. | 356/39 X |

OTHER PUBLICATIONS

Janssen, F. J., *Medicamundi*, vol. 17, No. 1 (1972), pp. 7–15.
Laing, R. A., et al., *I.E.E.E. Trans. on Biomed. Engng.*, vol:BME-22, No. 3, May 1975.

*Primary Examiner*—Kyle L. Howell

[57] ABSTRACT

A non-invasive method of objectively determining, in vivo, the rate of oxygen utilization in peripheral tissue by spectral measuring means, which involves isolating a segment of blood in the tissue with a clamp or tourniquet, and obtaining rapid, successive spectral curves of the oxyhemoglobin in the occluded area, to and from selected wavelengths of light, and measuring the time-space relationship between a rapidly moving portion of the spectral curve and a slower moving adjacent portion of the same curve, from the moment of occlusion, to establish a rate of reduction of the oxyhemoglobin in the tissue which is directly correlated to the rate of oxygen utilization.

5 Claims, 3 Drawing Figures

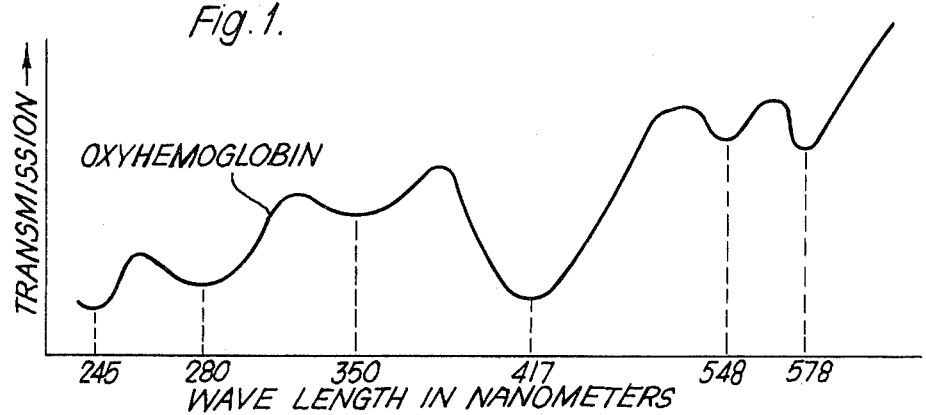
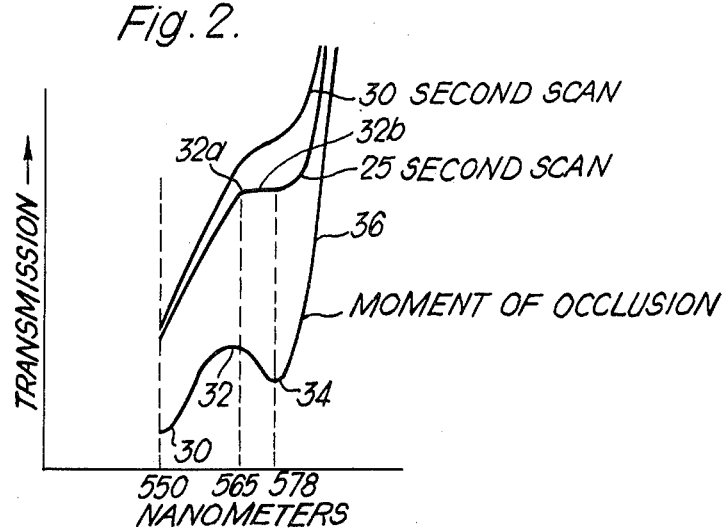
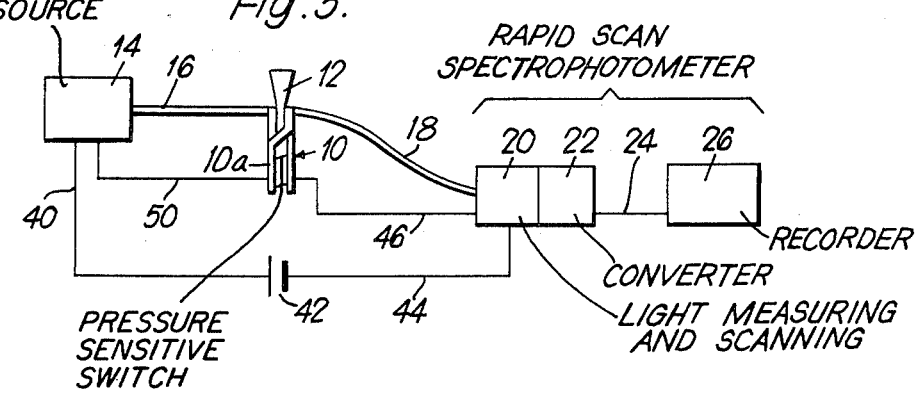

OBJECTIVE DETERMINATION OF THE RATE OF OXYGEN UTILIZATION IN PERIPHERAL TISSUE

This invention relates to the determination of the rate of oxygen utilization in the tissue, and more particularly to its determination by spectral means.

The spectral phenomena of oxyhemoglobin has been known since 1875, when it was reported by K. Vierordt in Physiologische Spectralanalysen Zeitrschrift fur Biologie, 1875, pp 187–198; 1878, pp 422–448. However, no extensive use has been made to utilize the phenomena which requires great subjective skill and visual acuity possessed by few persons. Thus the phenomena is practically unknown in the medical field, except for its application in oximetry for determining the approximate oxygen content during operative procedures.

The rate of oxygen utilization represents the summation of many chemical activities in the body; examples being the hormonal system, and the enzymes used in the oxidation-reduction process.

With an accurate and sensitive measurement of oxygen utilization, it is possible to determine that one or more of the multiple factors which contribute to body metabolism, are out of balance, and to evaluate the remedial procedures that should be initiated to locate and correct the imbalance.

Thus, if the change in the rate of oxygen utilization is in the direction of homeostatis, the diagnosis and procedure would appear to be relevant. If however, the rate is exacerbated or unchanged, the remedial procedure should be deemed to be valueless in correcting the imbalance.

Accordingly, the principal object of the invention is to provide a simple, direct, and non-invasive method for determining objectively, the rate of oxygen utilization in tissue using spectrometric means.

Other objects are to determine those points on the spectral curve for oxyhemoglobin, which under occlusion, show a rate of change greater than other adjacent points on the same curve; to provide a scan of the spectral curve for oxyhemoglobin, continuously repeated through selected areas, at selected time intervals, so that the time-space changes in the reproduced curves, indicate the relative changes in the oxygen content of the hemoglobin, for the specified period of time; and to select a point on the spectral curve for oxyhemoglobin which appears to be most sensitive to inner change for use as a standard for determining the rate of oxygen utilization.

These and other objects are achieved, and new results obtained, as will be evident from a consideration of the following description, claims, and drawing in which:

FIG. 1 is a spectral curve for oxyhemoglobin showing the relative light transmission for all wavelengths from about 240 to about 600 nanometers.

FIG. 2 shows successive spectral curves of oxyhemoglobin from the moment of tissue occlusion to the 30 second scan, in the 550–600 nanometer area.

FIG. 3 is a schematic diagram of a light transmitting and measuring apparatus that may be used to provide the rapid scan spectral curves for oxyhemoglobin illustrated in FIG. 2.

I employ for my purpose, an interdigital clamp 10, shown in FIG. 3. which is similar in nature to a hemostat, containing an aperture in the clamping jaws, to allow light to pass therethrough. The locking pressure of the clamp will isolate a segment of blood within the apertured area which may be about 5 mm in diameter, when the clamp is applied to the interdigital fold of skin on the hand. The pressure is sufficient to keep new blood from entering the isolated area or to leave, but insufficient to produce any physical discomfort or mental disturbance. The skin of the interdigital fold is shown as 12.

The light from source 14, is transmitted to the clamped area by optical pipe 16, and from the clamped area by pipe 18 to a light measuring and scanning device 20, employing a spectrometric means, which is capable of measuring the relative transmitted light values at various selected wavelengths. The transmitted light values are converted into electrical components and amplified sufficiently for measuring purposes by the converter 22, from which device the signals are fed into a display device such as an oscillograph or X-Y recorder 26.

A scan throughout the area from about 245 nanometers to about 600 of oxyhemoglobin is shown in FIG. 1. The apparatus will also show the scanned area between selected wavelengths and periodically rescan the selected area, desireably in one second or less time, depending on the accuracy desired.

Of all the sensitive areas of the oxyhemoglobin curve, showing a rate of change which is greater than the adjacent areas of the same curve during oxygen reduction, after occlusion, such as 245, 280, 350, 417, 548 and 578 nanometers, it appears that 578 is the most desireable for our purpose. Therefore the rapid scan technique shown in FIG. 2. illustrates the change in the spectral curve for oxyhemoglobin from the moment of occlusion, to the moment when the relative transmission has reached the same value for the 578 nanometer wavelength, as for the 565 nanometer wavelength.

In place of the interdigital clamp, a tourniquet may be used, about the upper arm or even around a finger. Instead of transmitted light, reflected light from the skin will similarly pick up the oxyhemoglobin especially if erythema is produced by rubbing the skin or by the use of chemicals.

In place of a scanning spectrophotometer, interference filters may be used having selected nanometer ratings. A recording spectrophotometer made by the American Optical Company, employed a mirror mounted on a vibrating reed. The reflected light from the mirror, scanned the spectrum with each oscillation of the reed, and produced a visual image of the spectral curve on an oscilloscope with each reed vibration. Thus a scan of one-sixtieth of a second is possible.

The time required for the oxyhemoglobin to be reduced from the position shown in FIG. 2, at the lowest point at the 578 curve starting from the moment of occlusion, namely 34, to reach the same level of the change as does the peak 32 of the same curve 30, is 25 seconds for the particular individual tested. This occurs when 32b reaches the same level as 32a. This time period for an individual is designated as the reduction time. It is also correlated to the rate of oxygen utilization by the tissue. It will be noted that the sensitive part of the curve, namely the portion designated as 34, shows a fast reduction beyond the point 32b, as is indicated in the 30 second scan where the point of inflexion of the curve is reversed.

In the space-time relationship uniquely set forth, it is possible to use a measured change in the relationship where instead of time being the variable, the time is constant and the space change is measured for a fixed period of time. This places a limitation on the instrument used, and is a more limited determination. As presently employed the time designation representing an inner change requirement of the oxyhemoglobin curve is independent of the instrument used, the thickness and character of the skin, and especially its pigmentation.

It has been confirmed that the rate of oxygen utilization is a measure of the individual's degree of homeostatis. A reduction time below 25 seconds appears to indicate some form of dysfunction. An increased efficiency in oxygen utilization is represented by a rate of utilization of 25 seconds or more, and readings have been taken to 70 seconds.

The test is an extremely sensitive one, since the body at rest and in motion will have different rates of oxygen utilization. Since the test is noninvasive, the adrenal shock caused by blood withdrawal does not enter into the reading and does not modify or destroy its accuracy.

Moreover, if an accellerated rate of oxygen utilization is found, for example of 18 seconds, and treatment is undertaken to correct the dysfunction, if the change in the rate of oxygen utilization is not in the direction of homeostasis, it can be assumed that the treatment is not adequate or even harmful. This applies to drug doses which may be effective only in specific amounts.

The foregoing method of measuring the rate of oxygen utilization is as simple as the use of a thermometer for reading body temperature. Like the thermometer, the reading merely discloses some interference in oxygen utilization. Unlike a thermometer, it is a far more sensitive measurement and will show a disfunction where a thermometer will show a normal reading. Moreover, it can be used to indicate the effectiveness of remedial procedures.

To insure safety of the sensitive instruments, and accuracy in reading, the clamp should be provided with electrical contacts and circuits to start the light source and the timing mechanism, only when the clamp is closed upon the tissue.

This can be accomplished by placing a pressure-sensitive electrical switch 52 between the extending arms 10a of clamp 10. When the clamp is compressed about the interdigital fold 12, the electrical circuit indicated by leads 50, 46, 44, and 40, powered by the battery 42 or current source, is closed, allowing the current to flow into the light source 14, and into the light measuring and scanning apparatus 20.

When the pressure on the interdigital fold is released, the pressure-sensitive switch will open the circuit, disconnecting the light source and the light measuring and scanning apparatus, preventing damage from the light beam passing directly into the light sensitive instruments, when the interdigital fold is removed from the clamp. Thus the light source is operative only when the clamp is compressed about the interdigital fold.

I have thus described my invention, but I desire it understood that it is not confined to the particular apparatus and methods shown and described, the same being merely illustrative, and that the invention may be carried out in other ways without departing from the spirit of my invention, and therefore, I claim the right to employ all equivalents coming within the scope of the appended claims, and by means of which objects of my invention are obtained, and new results accomplished, since the particular examples herein described are only some of the many that can be employed to obtain the desired objects and accomplish the results achieved.

I claim:

1. A non-invasive, spectrometric method of objectively determining in vivo, the rate of oxygen utilization in peripheral tissue, which comprises isolating a segment of blood in the tissue of the skin, and simultaneously and rapidly obtaining from the moment of blood isolation, the changing light coefficients of absorption for oxyhemoglobin in the isolated blood, at two adjacent wavelengths in which the coefficients of absorption of one wavelength, has a faster rate of change than the other, and determining the rate of change of one light coefficient with respect to the other.

2. The method of claim 1, in which the selected wavelengths of oxyhemoglobin are taken from adjacent wavelengths at the 245, 280, 350, 417, 548 and 578 nm.

3. The method of claim 1, in which the adjacent wavelengths are about 565 and 578 nm.

4. The method of claim 1, in which the rate of change of one light coefficient with respect to the other is measured by the time required from the moment of blood isolation, for one coefficient of absorption to equal that of the other.

5. The method of claim 1, in which the rate of change of one light coefficient with respect to the other is measured by the time required from the moment of blood isolation, for the coefficient of absorption at 578 nm, to equal the coefficient of absorption at about 565 nm.

* * * * *